(12) United States Patent
Carlson et al.

(10) Patent No.: US 10,233,207 B2
(45) Date of Patent: *Mar. 19, 2019

(54) CRYSTALLINE FORM OF NICOTINAMIDE RIBOSIDE

(71) Applicant: W. R. Grace & Co.—Conn., Columbia, MD (US)

(72) Inventors: Erik C. Carlson, Albany, OR (US); Michael C. Standen, Salem, OR (US); Westin H. Morrill, Grayslake, IL (US)

(73) Assignee: W. R. Grace & Co.—Conn., Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/791,097

(22) Filed: Oct. 23, 2017

(65) Prior Publication Data

US 2018/0086783 A1 Mar. 29, 2018

Related U.S. Application Data

(63) Continuation of application No. 15/328,664, filed as application No. PCT/US2015/041956 on Jul. 24, 2015.

(60) Provisional application No. 62/028,702, filed on Jul. 24, 2014.

(51) Int. Cl.
 *C07H 19/048* (2006.01)
(52) U.S. Cl.
 CPC ........ *C07H 19/048* (2013.01); *C07B 2200/13* (2013.01)
(58) Field of Classification Search
 None
 See application file for complete search history.

(56) References Cited

U.S. PATENT DOCUMENTS

| | | | |
|---|---|---|---|
| 3,708,394 A | 1/1973 | Nakayama | |
| 3,728,111 A | 4/1973 | Stromblad et al. | |
| 7,776,326 B2 | 8/2010 | Millbrandt | |
| 8,106,184 B2 | 1/2012 | Sauve | |
| 8,114,626 B2 | 2/2012 | Brenner | |
| 8,197,807 B2 | 6/2012 | Brenner | |
| 8,217,006 B2 | 7/2012 | Stamler | |
| 8,383,086 B2 | 2/2013 | Brenner | |
| 8,399,489 B2 | 3/2013 | Basarab | |
| 8,481,711 B2 | 7/2013 | Kaminishi | |
| 8,507,251 B2 | 8/2013 | Greenstein | |
| 9,000,147 B2 | 4/2015 | Sauve | |
| 2004/0266723 A1 | 12/2004 | Otto | |
| 2005/0020587 A1 | 1/2005 | Bailey et al. | |
| 2005/0267023 A1 | 12/2005 | Sinclair et al. | |
| 2006/0229265 A1 | 10/2006 | Milburn et al. | |
| 2007/0149466 A1 | 6/2007 | Milburn | |
| 2007/0166296 A1 | 7/2007 | Burke | |
| 2007/0248590 A1 | 10/2007 | Milne | |
| 2008/0146569 A1 | 6/2008 | Blake et al. | |
| 2010/0015072 A1 | 1/2010 | Polla | |
| 2010/0047177 A1 | 2/2010 | Milbrandt | |
| 2011/0065662 A1 | 3/2011 | Rinsch | |
| 2011/0306597 A1 | 12/2011 | Crawforth et al. | |
| 2012/0022013 A1 | 1/2012 | Sinclair | |
| 2012/0107888 A1 | 5/2012 | Schmalisch | |
| 2012/0172584 A1 | 7/2012 | Sauve et al. | |
| 2012/0328526 A1 | 12/2012 | Kristian | |
| 2012/0329748 A1 | 12/2012 | Sauve et al. | |
| 2013/0059384 A1 | 3/2013 | Tilly | |
| 2013/0165398 A1 | 6/2013 | Huber | |
| 2014/0045874 A1 | 2/2014 | Tolleth | |
| 2014/0065099 A1 | 3/2014 | Alvarez | |
| 2014/0221319 A1 | 8/2014 | Sinclair | |
| 2014/0256760 A1 | 9/2014 | Tolleth | |
| 2015/0056274 A1 | 2/2015 | Zemel | |
| 2015/0118169 A1 | 4/2015 | Hakozaki | |
| 2015/0132280 A1 | 5/2015 | Lopez | |
| 2015/0133396 A1 | 5/2015 | Sinclair | |
| 2015/0174148 A1 | 6/2015 | Brown | |
| 2015/0175645 A1 | 6/2015 | Milburn | |
| 2015/0297508 A1 | 10/2015 | Andriette | |
| 2016/0008329 A1 | 1/2016 | Zemel | |

FOREIGN PATENT DOCUMENTS

| | | |
|---|---|---|
| EP | 0981534 A2 | 3/2006 |
| KR | 1020150050406 | 5/2015 |
| WO | WO2007/136744 | 11/2007 |
| WO | WO2011/005289 | 1/2011 |
| WO | WO2013/085555 A3 | 6/2013 |
| WO | WO2014/059029 | 4/2014 |
| WO | WO2014/111906 | 7/2014 |
| WO | WO2015/064988 | 5/2015 |
| WO | WO2015/066382 | 5/2015 |
| WO | WO2015/099842 | 7/2015 |
| WO | WO2015/138969 | 9/2015 |
| WO | WO2015/138986 | 9/2015 |
| WO | 2015186068 A1 | 12/2015 |
| WO | 2015186114 A1 | 12/2015 |
| WO | WO2016/011360 | 1/2016 |

OTHER PUBLICATIONS

F. Schlenk; Nicotinamide Riboside; Jul. 3, 1943; pp. 93-103.

*Primary Examiner* — Layla D Berry

(74) *Attorney, Agent, or Firm* — Baker & Hostetler LLP

(57) ABSTRACT

Provided are crystalline forms of nicotinamide riboside, including a Form I of nicotinamide riboside chloride according to formula (I). Also disclosed are pharmaceutical compositions comprising the crystalline Form I of nicotinamide riboside chloride, and methods of producing such pharmaceutical compositions. In other aspects, the present disclosure pertains to methods comprising administering to a subject the crystalline Form I of nicotinamide riboside chloride. The present disclosure also provides methods of preparing the crystalline Form I of nicotinamide riboside chloride. Also provided are a crystalline Form I of nicotinamide riboside chloride that is prepared according to any of the disclosed methods for preparing the crystalline Form I.

23 Claims, 10 Drawing Sheets

CRYSTALLINE FORM OF NICOTINAMIDE RIBOSIDE

CROSS-REFERENCE TO RELATED APPLICATIONS

This application is a continuation of U.S. Ser. No. 15/328,664, filed Jan. 24, 2017, which is a National Stage Application filed under 35 U.S.C. 371 of International Application No. PCT/US2015/041956 filed Jul. 24, 2015, which claims the benefit of U.S. Provisional Patent Application No. 62/028,702, filed on Jul. 24, 2014, the entire contents of which are incorporated herein by reference.

TECHNICAL FIELD

The present disclosure relates to crystalline forms of nicotinamide riboside, and in particular, nicotinamide riboside chloride, as well as compositions containing the crystalline form and methods for using the crystalline form.

BACKGROUND

Crystalline forms of useful molecules can have advantageous properties relative to the amorphous form of such molecules. For example, crystal forms are often easier to handle and process, for example, when preparing compositions that include the crystal form. Crystalline forms typically have greater storage stability and are more amenable to purification. The use of a crystalline form of a pharmaceutically useful compound can also improve the performance characteristics of a pharmaceutical product that includes the compound. Obtaining the crystalline form also serves to enlarge the repertoire of materials that formulation scientists have available for formulation optimization, for example by providing a product with different properties, e.g., better processing or handling characteristics, improved dissolution profile, or improved shelf-life.

Nicotinamide riboside (CAS Number 1341-23-7) is a precursor to nicotinamide adenine dinucleotide (NAD) and represents a source of vitamin B3. Recent studies have indicated that novel health benefits may result from ingesting nicotinamide riboside in larger quantities than is found naturally in foods. For example, nicotinamide riboside has been implicated in raising tissue NAD concentrations and in eliciting insulin sensitivity and enhancement of sirtuin functions. See Chi Y, et al., Curr Opin Clin Nutr Metab Care. 2013 November; 16(6):657-61. Its ability to increase NAD production indicates that nicotinamide riboside can also increase mitochondrial health, stimulate mitochondrial function, and induce creation of new mitochondria. Additional studies with nicotinamide riboside in models of Alzheimer's disease have suggested that the molecule is bioavailable to the brain and provides neuroprotective effects, likely by stimulation of brain NAD synthesis. Id. Furthermore, a 2012 study observed that mice on a high-fat diet that was supplemented with nicotinamide riboside gained 60% less weight than mice eating the same high-fat diet without nicotinamide riboside.

Nicotinamide riboside chloride (3-carbamoyl-1-[(2R,3R,4S5R)-3,4-dihydroxy-5-(hydroxymethypoxolan-2-yl]-pyrin-1-ylium chloride; also referred to as 1-(($\beta$-D-Ribofuranosyl)nicotinamide chloride) is a known salt form of nicotinamide riboside and has the structure depicted below:

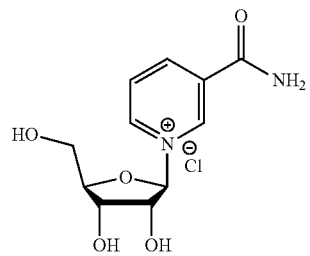

Despite the useful attributes of nicotinamide riboside and its chloride salt, for example, for use in pharmaceuticals or nutritional supplements, and the benefits of providing such molecules in an ordered form, improvements are generally desired.

SUMMARY

The present disclosure pertains to crystalline forms of nicotinamide riboside, including a Form I of nicotinamide riboside chloride according to formula I

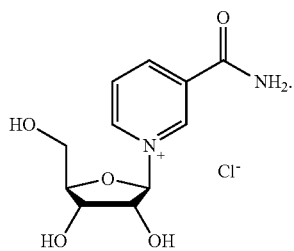

(I)

Also disclosed are pharmaceutical compositions comprising the crystalline Form I of nicotinamide riboside chloride, and methods of producing such pharmaceutical compositions.

In other aspects, the present disclosure pertains to methods comprising administering to a subject the crystalline Form I of nicotinamide riboside chloride.

The present disclosure also provides methods of preparing the crystalline Form I of nicotinamide riboside chloride. Also provided are a crystalline Form I of nicotinamide riboside chloride that is prepared according to any of the disclosed methods for preparing the crystalline Form I.

DETAILED DESCRIPTION OF ILLUSTRATIVE EMBODIMENTS

Figure 1:
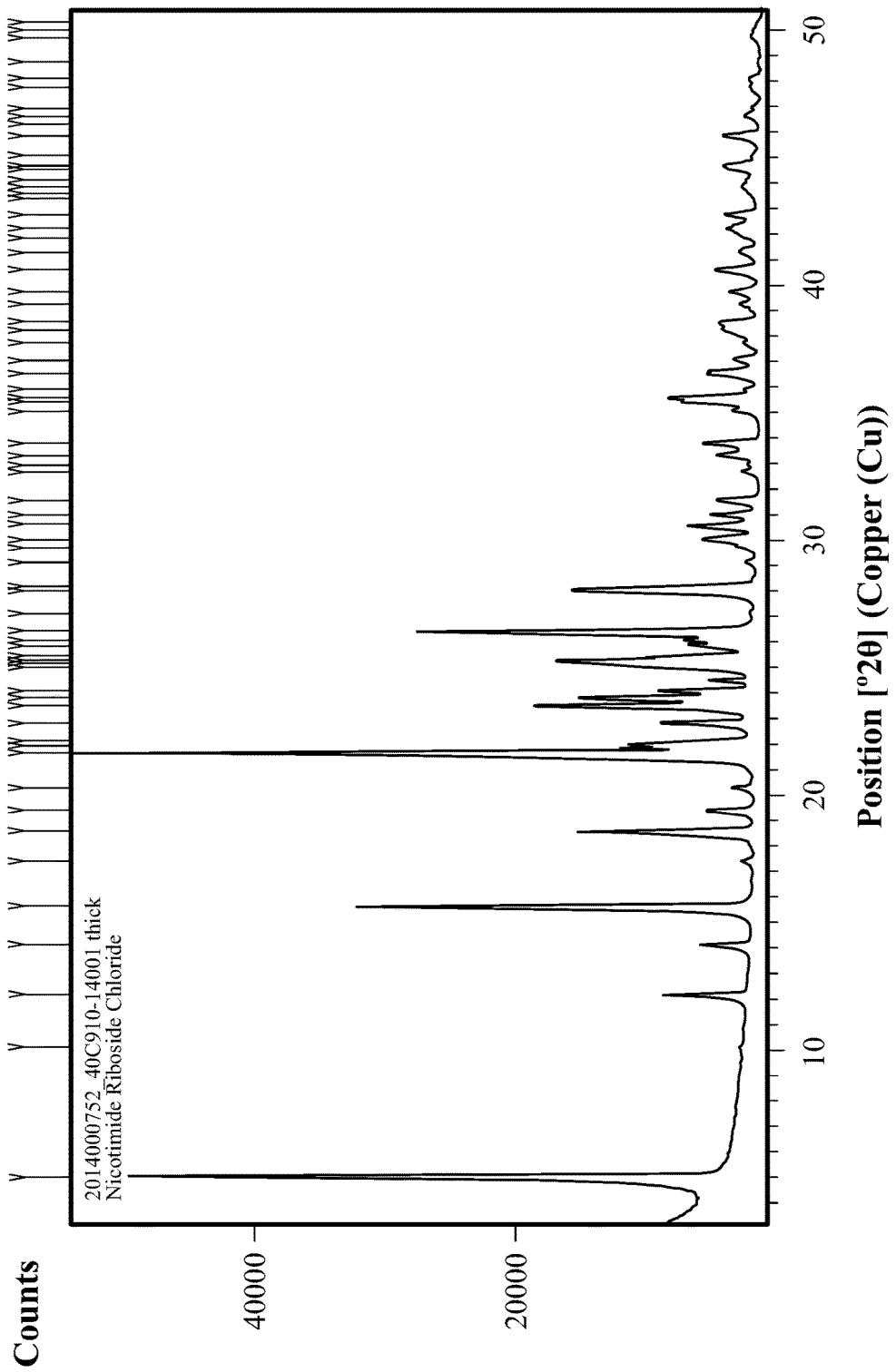
FIG. 1 provides an X-ray powder diffraction pattern for crystalline nicotinamide riboside chloride.

The present invention may be understood more readily by reference to the following detailed description taken in connection with the accompanying figures and examples, which form a part this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The entire disclosures of each patent, patent application, and publication cited or described in this document are hereby incorporated herein by reference.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a solvent" is a reference to one or more of such solvents and equivalents thereof known to those skilled in the art, and so forth. Furthermore, when indicating that a certain element "may be" X, Y, or Z, it is not intended by such usage to exclude in all instances other choices for the element.

When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like. In addition, when a list of alternatives is positively provided, such a listing can also include embodiments where any of the alternatives may be excluded. For example, when a range of "1 to 5" is described, such a description can support situations whereby any of 1, 2, 3, 4, or 5 are excluded; thus, a recitation of "1 to 5" may support "1 and 3-5, but not 2", or simply "wherein 2 is not included."

As used herein, the terms "treatment" or "therapy" (as well as different word forms thereof) includes preventative (e.g., prophylactic), curative, or palliative treatment. Such preventative, curative, or palliative treatment may be full or partial. For example, complete elimination of unwanted symptoms, or partial elimination of one or more unwanted symptoms would represent "treatment" as contemplated herein.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Provided herein are crystalline forms of nicotinamide riboside chloride. Although nicotinamide riboside and its chloride salt are well known among those of ordinary skill in the art in their amorphous forms and have numerous uses deriving, for example, from the ability of such molecules to increase NAD production, the present disclosure is directed to these molecules in a crystalline form. Crystalline forms of nicotinamide riboside have advantageous properties, including chemical purity, flowability, solubility, morphology or crystal habit, and stability (such as storage stability, stability to dehydration, stability to polymorphic conversion, low hygroscopicity, and low content of residual solvents).

A crystal form may be referred to herein as being characterized by graphical data substantially "as depicted in" a Figure. Such data include, for example, powder X-ray diffractograms and solid state IR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

The present disclosure pertains to crystalline forms of nicotinamide riboside, including a Form I of nicotinamide riboside chloride according to formula I

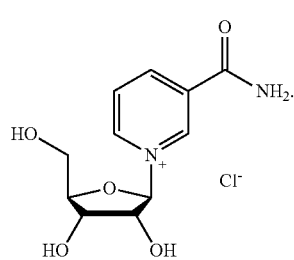

The crystalline Form I may be characterized by a powder X-ray diffraction pattern having peaks at 5.1, 15.7, and 21.7 degrees two theta±0.2 degrees two theta. The crystalline Form I may also or alternatively be characterized by a powder X-ray diffraction pattern having peaks at 5.1, 15.7, 21.7, 23.5, and 26.4 degrees two theta±0.2 degrees two theta. The crystalline Form I may also or alternatively be characterized by a powder X-ray diffraction pattern having peaks at 5.1, 15.7, 18.6, 21.7, 23.5, 26.4, and 28.0 degrees two theta±0.2 degrees two theta.

In other embodiments, the crystalline Form I may be characterized by a powder X-ray diffraction pattern substantially as shown in FIG. 1. The crystalline Form I may also or alternatively be characterized by a powder X-ray diffraction pattern having peaks substantially as provided in Table 1, below, ±0.2 degrees two theta.

TABLE 1

| No. | Pos. [° 2Th.] | d-spacing [Å] | Height [cts] | I/Imax |
|---|---|---|---|---|
| 1 | 5.0847 | 17.36541 | 29562 | 87% |
| 2 | 10.09 | 8.75955 | 158 | 0% |
| 3 | 12.194 | 7.25232 | 4234 | 12% |
| 4 | 14.141 | 6.25817 | 2433 | 7% |
| 5 | 15.662 | 5.65364 | 19978 | 59% |
| 6 | 17.4 | 5.09227 | 576 | 2% |
| 7 | 18.573 | 4.77348 | 9176 | 27% |
| 8 | 19.415 | 4.56839 | 2563 | 8% |
| 9 | 20.35 | 4.36098 | 831 | 2% |
| 10 | 21.685 | 4.09491 | 33878 | 100% |
| 11 | 21.919 | 4.05175 | 4369 | 13% |
| 12 | 22.148 | 4.01031 | 5971 | 18% |
| 13 | 22.842 | 3.89009 | 4521 | 13% |
| 14 | 23.519 | 3.77954 | 10585 | 31% |
| 15 | 23.825 | 3.73181 | 8674 | 26% |
| 16 | 24.103 | 3.68936 | 4752 | 14% |
| 17 | 24.47 | 3.63519 | 434 | 1% |
| 18 | 25.05 | 3.55221 | 5408 | 16% |
| 19 | 25.149 | 3.53825 | 107 | 0% |
| 20 | 25.244 | 3.52517 | 8758 | 26% |
| 21 | 25.438 | 3.4987 | 4768 | 14% |
| 22 | 25.836 | 3.44564 | 2741 | 8% |
| 23 | 26.035 | 3.41975 | 2662 | 8% |
| 24 | 26.43 | 3.36953 | 18356 | 54% |
| 25 | 28.016 | 3.1823 | 9628 | 28% |
| 26 | 28.164 | 3.16597 | 3910 | 12% |
| 27 | 29.13 | 3.06327 | 552 | 2% |
| 28 | 29.7 | 3.00557 | 799 | 2% |
| 29 | 30.02 | 2.97428 | 2725 | 8% |
| 30 | 30.628 | 2.91661 | 3400 | 10% |
| 31 | 30.996 | 2.88284 | 2421 | 7% |
| 32 | 31.576 | 2.8312 | 2259 | 7% |
| 33 | 32.658 | 2.73983 | 850 | 3% |
| 34 | 32.95 | 2.71631 | 431 | 1% |
| 35 | 33.295 | 2.6888 | 1887 | 6% |
| 36 | 33.8 | 2.64976 | 2964 | 9% |
| 37 | 35.06 | 2.55763 | 1199 | 4% |
| 38 | 35.426 | 2.53179 | 3426 | 10% |
| 39 | 35.586 | 2.5208 | 4384 | 13% |
| 40 | 35.92 | 2.49794 | 500 | 1% |
| 41 | 36.534 | 2.45752 | 2679 | 8% |
| 42 | 37.074 | 2.42298 | 1143 | 3% |
| 43 | 37.616 | 2.3893 | 536 | 2% |
| 44 | 38.13 | 2.35799 | 1057 | 3% |
| 45 | 38.56 | 2.33306 | 1731 | 5% |
| 46 | 39.218 | 2.29527 | 980 | 3% |
| 47 | 39.729 | 2.26696 | 1467 | 4% |
| 48 | 40.624 | 2.21904 | 2257 | 7% |
| 49 | 41.32 | 2.18334 | 890 | 3% |
| 50 | 42.2 | 2.13986 | 1389 | 4% |
| 51 | 42.76 | 2.11298 | 1812 | 5% |
| 52 | 43.79 | 2.06588 | 681 | 2% |
| 53 | 44.58 | 2.03105 | 1628 | 5% |
| 54 | 44.68 | 2.02661 | 1483 | 4% |
| 55 | 45.083 | 2.00939 | 363 | 1% |
| 56 | 45.857 | 1.97724 | 2012 | 6% |
| 57 | 46.63 | 1.9463 | 858 | 3% |
| 58 | 46.95 | 1.93366 | 455 | 1% |
| 59 | 47.67 | 1.90628 | 518 | 2% |
| 60 | 48.08 | 1.89074 | 630 | 2% |
| 61 | 49.69 | 1.83344 | 442 | 1% |
| 62 | 49.96 | 1.82422 | 354 | 1% |
| 63 | 50.3 | 1.81235 | 222 | 1% |

Figure 2:
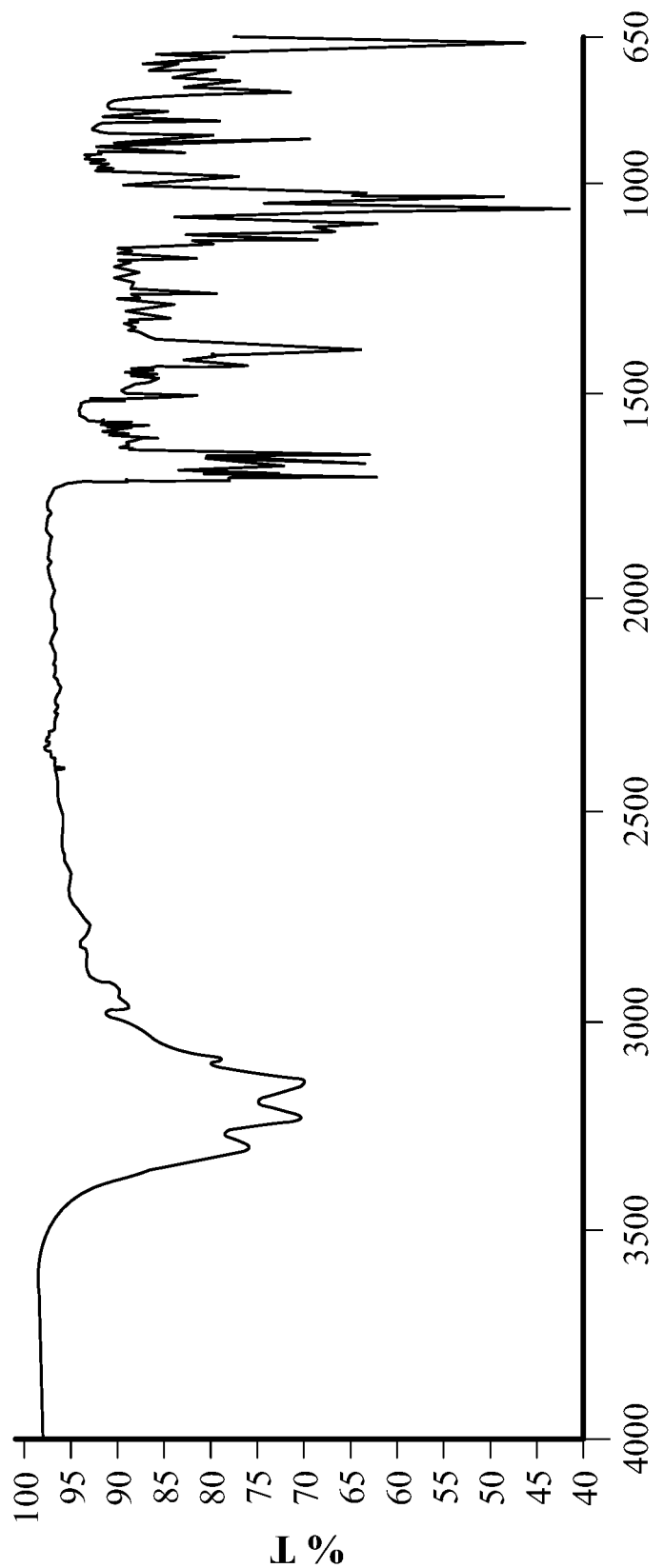
FIG. 2 shows a solid state IR spectrum of crystalline nicotinamide riboside chloride.

The crystalline Form I of nicotinamide riboside chloride may also or alternatively be characterized by a solid-state IR spectrum having peaks at 671.7, 1035.6, and, 1061.8 cm$^{-1}$±0.2 cm$^{-1}$. The crystalline Form I of nicotinamide riboside chloride may also or alternatively be characterized by a solid-state IR spectrum having peaks at 671.7, 1035.6, 1061.8, 1398.9, and 1649.3 cm$^{-1}$±0.2 cm$^{-1}$. In certain embodiments, the crystalline Form I of nicotinamide riboside chloride may be characterized by a solid-state IR spectrum substantially as shown in FIG. 2. In further embodiments, the crystalline Form I of nicotinamide riboside chloride may be characterized by a solid-state IR spectrum having peaks substantially as provided in Table 2, below, ±0.2 cm$^{-1}$.

TABLE 2

| IR (cm$^{-1}$) |
|---|
| 3307.91 |
| 3236.09 |
| 3150.27 |
| 2967.14 |
| 1702.35 |
| 1667.56 |
| 1649.34 |
| 1611.33 |
| 1582.94 |
| 1468.53 |
| 1436.77 |
| 1398.92 |
| 1324.43 |
| 1291.92 |
| 1263.29 |
| 1215.24 |
| 1179.00 |
| 1148.84 |
| 1135.31 |
| 1110.95 |
| 1101.18 |
| 1061.82 |

TABLE 2-continued

| IR (cm$^{-1}$) |
|---|
| 1035.62 |
| 986.71 |
| 926.55 |
| 899.63 |
| 852.33 |
| 830.75 |
| 779.75 |
| 760.46 |
| 734.93 |
| 705.48 |
| 671.72 |
| 3307.91 |
| 3236.09 |
| 3150.27 |
| 2967.14 |
| 1702.35 |
| 1667.56 |
| 1649.34 |
| 1611.33 |
| 1582.94 |
| 1468.53 |
| 1436.77 |
| 1398.92 |
| 1324.43 |
| 1291.92 |
| 1263.29 |
| 1215.24 |
| 1179.00 |
| 1148.84 |
| 1135.31 |
| 1110.95 |
| 1101.18 |
| 1061.82 |
| 1035.62 |
| 986.71 |
| 926.55 |
| 899.63 |
| 852.33 |
| 830.75 |
| 779.75 |
| 760.46 |
| 734.93 |
| 705.48 |
| 671.72 |

Figure 4:
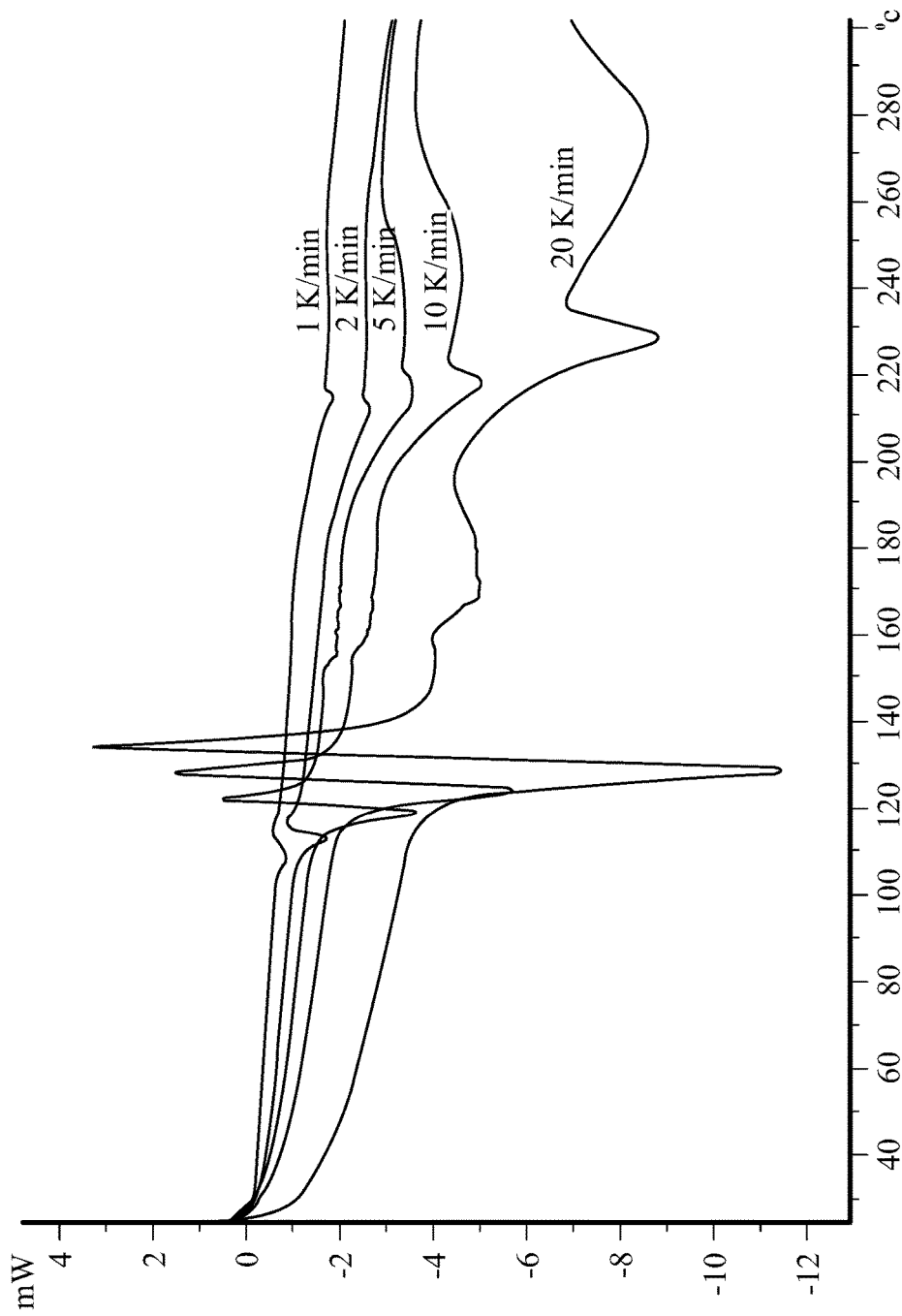
FIG. 4 provides DSC thermograms for crystalline Form I of nicotinamide riboside chloride as measured for each of the tested heating rates.

Another embodiment relates to a crystalline Form I of nicotinamide riboside chloride that has a DSC thermogram substantially as shown in FIG. 4.

In another embodiment, crystalline Form I of nicotinamide riboside chloride is characterized by a DSC thermogram obtained using a heating rate of 10 K/min comprising an endothermic event with an onset temperature of 119° C.±2° C. In certain instances, the crystalline Form I of nicotinamide riboside chloride is characterized by a DSC thermogram obtained using a heating rate of 10 K/min comprising an endothermic event with an onset temperature of 118.8° C.±2° C.

In other embodiments, crystalline Form I of nicotinamide riboside chloride is characterized by a DSC thermogram obtained using a heating rate of 1 K/min comprising an endothermic event with an onset temperature of 104° C.±2° C., a peak temperature of 108° C.±2° C., or both.

In other embodiments, crystalline Form I of nicotinamide riboside chloride is characterized by a DSC thermogram obtained using a heating rate of 2 K/min comprising an endothermic event with an onset temperature of 109° C.±2° C., a peak temperature of 113° C.±2° C., or both.

In other embodiments, crystalline Form I of nicotinamide riboside chloride is characterized by a DSC thermogram obtained using a heating rate of 5 K/min comprising an endothermic event with an onset temperature of 114° C.±2° C., a peak temperature of 118° C.±2° C., or both.

In still another embodiment, the crystalline Form I of nicotinamide riboside chloride is characterized by a DSC thermogram obtained using a heating rate of 10 K/min comprising an endothermic event with a peak temperature of 123° C.±2° C.

In a further embodiment, the crystalline Form I of nicotinamide riboside chloride is characterized by a DSC thermogram obtained using a heating rate of 10 K/min comprising an onset temperature of 119° C.±2° C., an endothermic event with a peak temperature of 123° C.±2° C., or both.

In other embodiments, crystalline Form I of nicotinamide riboside chloride is characterized by a DSC thermogram obtained using a heating rate of 20 K/min comprising an endothermic event with an onset temperature of 122° C.±2° C., a peak temperature of 128° C.±2° C., or both.

It is well known that the DSC onset and peak temperatures as well as energy values may vary due to, for example, the purity of the sample and sample size and due to instrumental parameters, especially the temperature scan rate. Hence the DSC data presented are not to be taken as absolute values. A person skilled in the art can set up instrumental parameters for a Differential scanning calorimeter so that data comparable to the data presented here can be collected according to standard methods, for example those described in Milne, G. W. H. et al (1996), Differential Scanning calorimetry, Springer, Berlin.

Figure 7A:
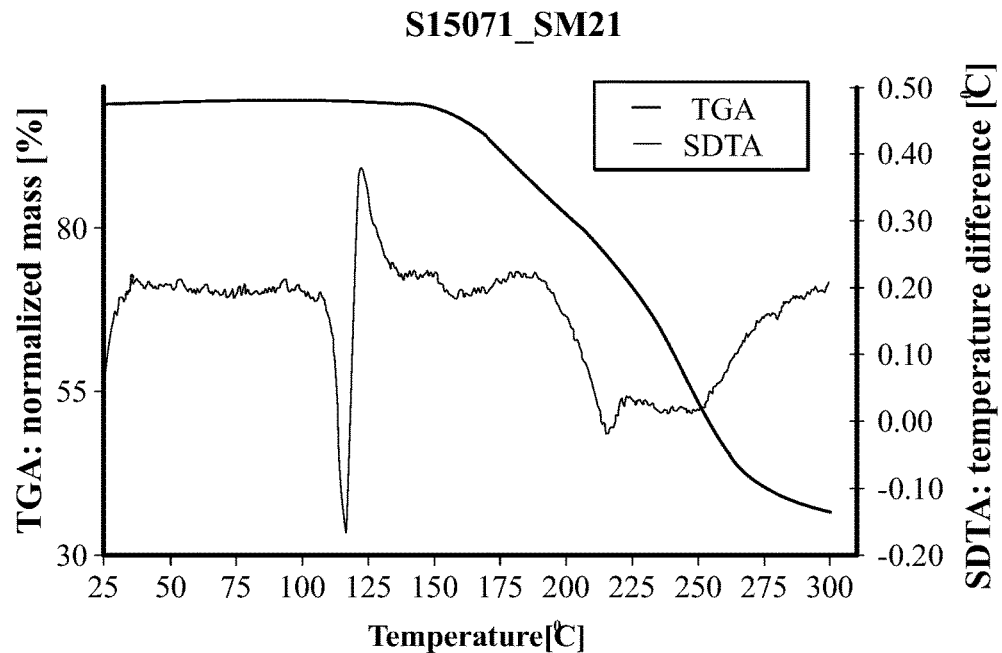
FIG. 7A shows a TGA/SDTA thermogram for crystalline Form I of nicotinamide riboside chloride.

One embodiment of the present invention pertains to a crystalline Form I of nicotinamide riboside chloride that has a TGA/SDTA thermogram substantially as shown in FIG. 7A.

The present disclosure also provides a crystalline Form I of nicotinamide riboside chloride that is characterized by a TGA/SDTA thermogram comprising an endothermic event at 116° C.±2° C. and a mass loss of about 0.4%. The present disclosure also provides a crystalline Form I of nicotinamide riboside chloride that is characterized by a TGA/SDTA thermogram comprising an endothermic event at 116.3° C.±2° C. and a mass loss of 0.36%.

Figure 8A:
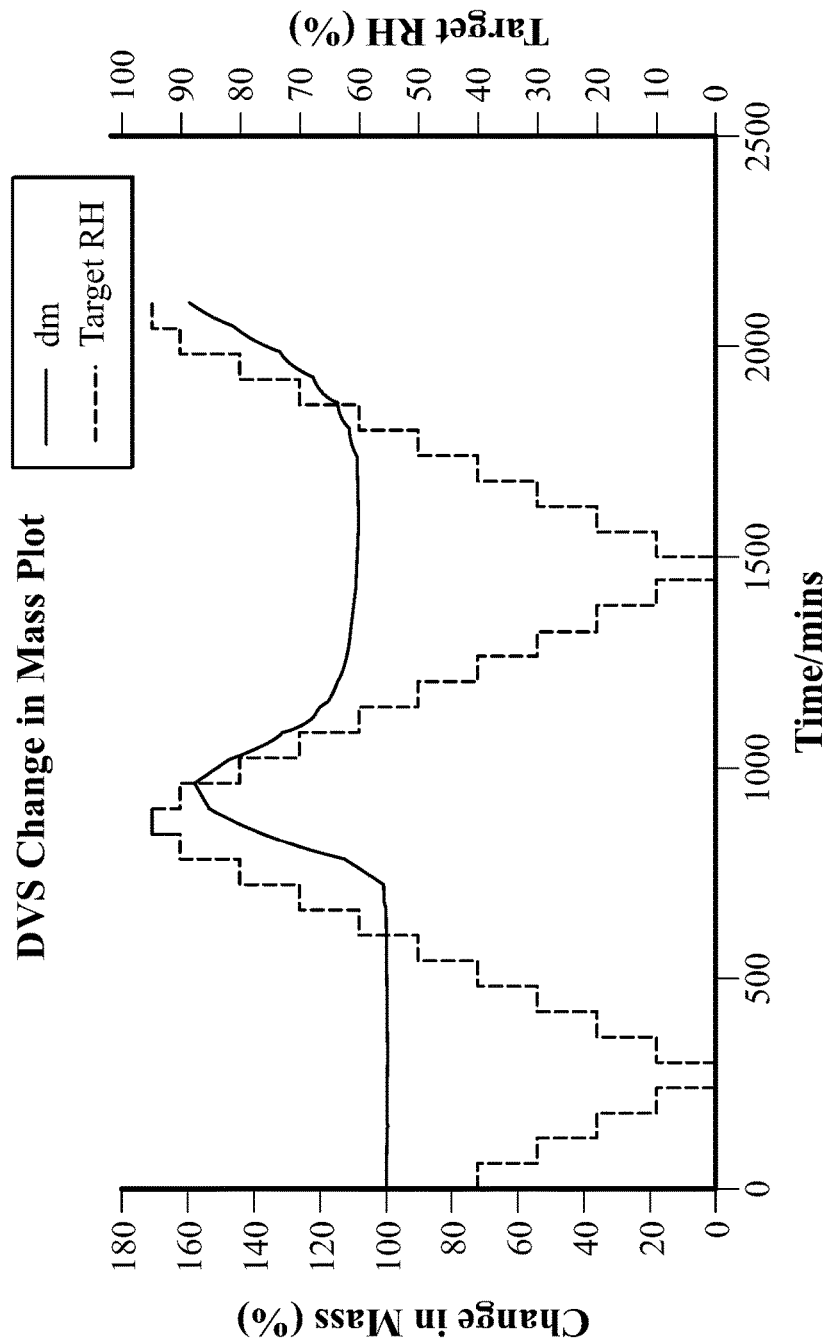
FIG. 8A provides a DVS change in mass plot for a sample of the crystalline Form I of nicotinamide riboside chloride, and FIG. 8B provides a DVS isotherm plot for a sample of the crystalline Form I of nicotinamide riboside chloride.
Figure 8B:
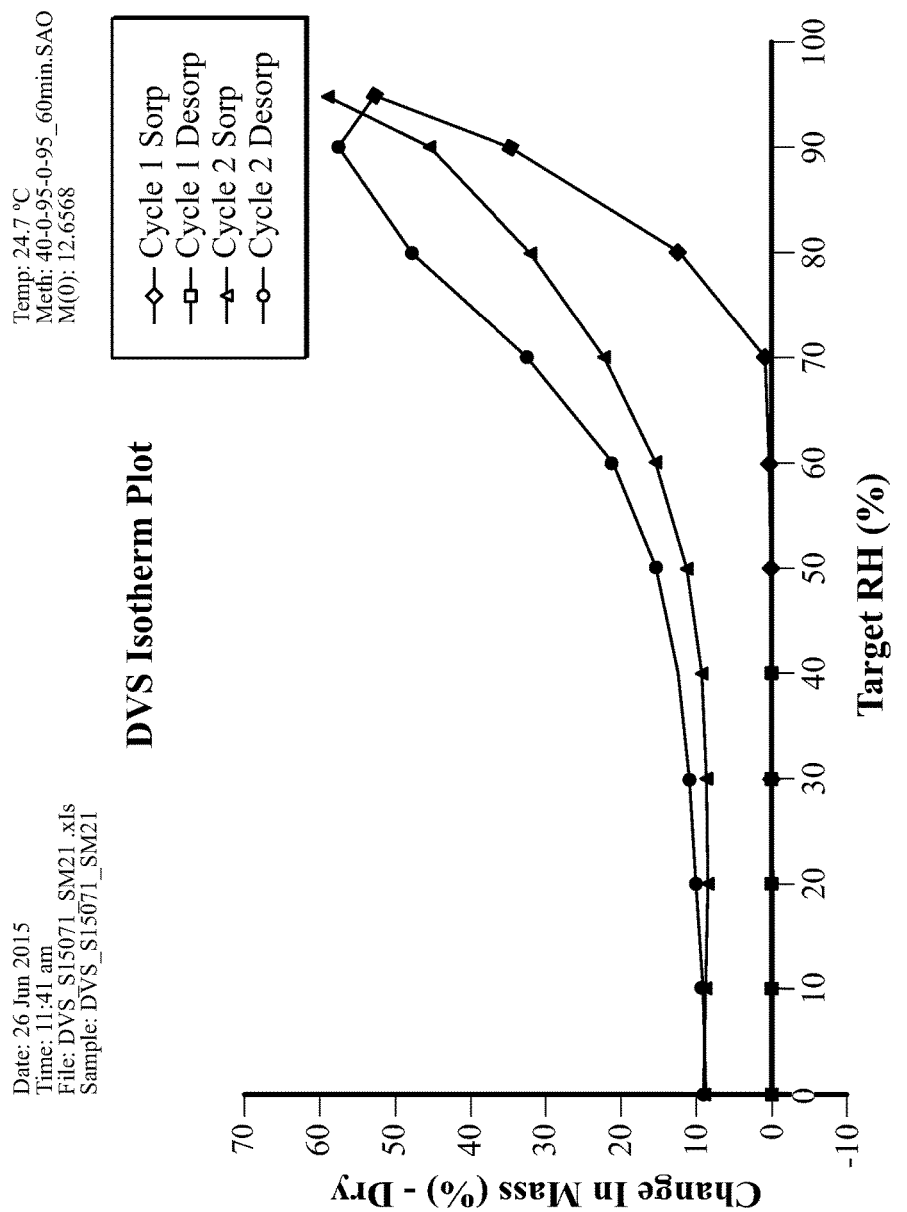

Also disclosed are a crystalline Form I of nicotinamide riboside chloride that is characterized by a DVS change in mass plot substantially as shown in FIG. 8A. In another embodiment, the crystalline Form I of nicotinamide riboside chloride that is characterized by a DVS isotherm plot substantially as shown in FIG. 8B.

In another aspect, the present disclosure provides a crystalline Form I of nicotinamide riboside chloride that is characterized by a water vapor sorption isotherm showing a water uptake of not more than about 0.5 wt % at a relative humidity of up to 60%. In another embodiment, the crystalline Form I of nicotinamide riboside chloride is characterized by a water vapor sorption isotherm showing a water uptake of not more than about 0.5 wt %, preferably not more than about 1.0 wt %, at a relative humidity of up to 70%.

Figure 3A:
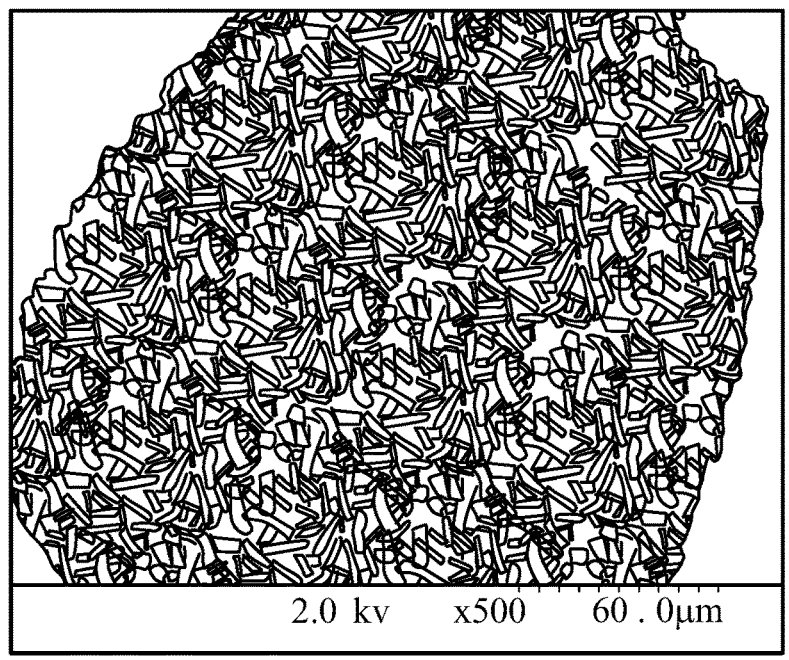
FIG. 3A is a rendering of a Scanning Electron Microscopy (SEM) image of a first morphology of crystalline nicotinamide riboside chloride.
Figure 3B:
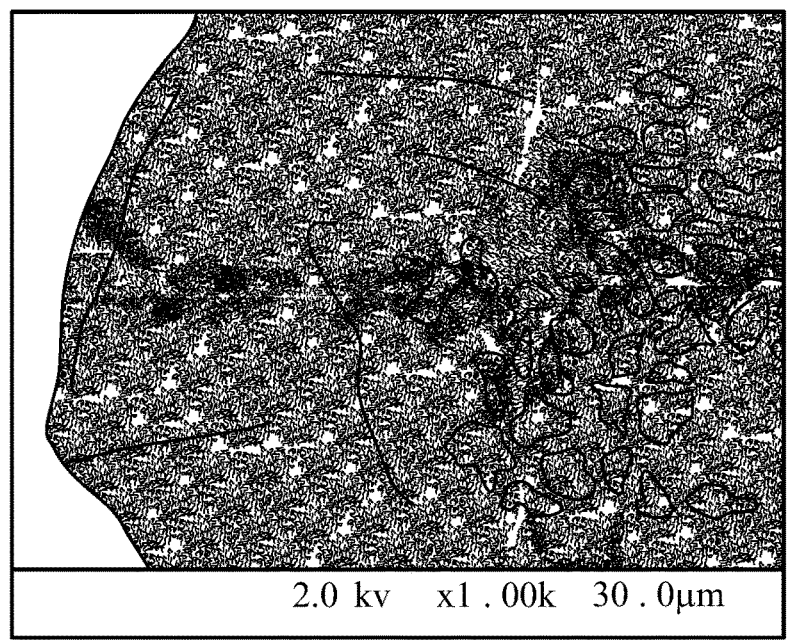
FIG. 3B is a rendering of an SEM image of a second morphology of crystalline nicotinamide riboside chloride.

The instant crystalline Form I of nicotinamide riboside chloride may be provided in one of several different morphologies. For example, the crystalline material may exist in a morphology having a bulk density of about 0.25 to about 0.4 g/mL, or may exist in a morphology having a bulk density of about 0.40 to about 0.65 g/mL. The present disclosure also relates to mixtures of at least these two morphologies in any proportion. FIG. 3A depicts a Scanning Electron Microscopy (SEM) image of the inventive crystalline nicotinamide riboside chloride in a morphology having a bulk density of about 0.25 to about 0.4 g/mL, and FIG. 3B depicts a Scanning Electron Microscopy (SEM) image of the inventive crystalline nicotinamide riboside chloride in a morphology having a bulk density of about 0.40 to about 0.65 g/mL. The present inventors have discovered that the morphology of crystalline nicotinamide chloride having a bulk density of about 0.25 to about 0.4 g/mL is more stable to degradation via oxygen or water absorption. This morphology also appears to provide the product with a slightly higher purity as well. Because of the purity, stability, and color variations in the other morphology (the morphology having a bulk density of about 0.40 to about 0.65 g/mL), in at least some instances a preference exists for the crystalline nicotinamide chloride having a bulk density of about 0.25 to about 0.4 g/mL as it appears to produce higher quality product with more consistency.

In some embodiments, the crystalline Form I of nicotinamide riboside chloride is at least partially hydrated, and in other embodiments, the crystalline Form I of nicotinamide riboside chloride is anhydrous.

The present disclosure also pertains to pharmaceutical compositions comprising the crystalline Form I of nicotinamide riboside chloride. The pharmaceutical composition may comprise the crystalline Form I of nicotinamide riboside chloride in any of the embodiments described above, and a pharmaceutically acceptable excipient. The pharmaceutical composition should include a therapeutically effective amount of the crystalline Form I of nicotinamide riboside chloride.

As used herein, the phrase "therapeutically effective amount" refers to the amount of active compound that elicits the biological or medicinal response that is being sought in a tissue, system, animal, individual or human by a researcher, veterinarian, medical doctor or other clinician, which includes one or more of the following:

(1) preventing the disease or condition; for example, preventing a disease, condition or disorder in an individual who may be predisposed to the disease, condition or disorder but does not yet experience or display the pathology or symptomatology of the disease;

(2) inhibiting the disease or condition; for example, inhibiting a disease, condition or disorder in an individual who is experiencing or displaying the pathology or symptomatology of the disease, condition or disorder (i.e., including arresting further development of the pathology and/or symptomatology); and (3) ameliorating the disease or condition; for example, ameliorating a disease, condition or disorder in an individual who is experiencing or displaying the pathology or symptomatology of the disease, condition or disorder (i.e., including reversing the pathology and/or symptomatology).

The present compositions may be formulated for any type of administration. For example, the compositions may be formulated for administration orally, topically, parenterally, enterally, or by inhalation. The crystalline Form I may be formulated for neat administration, or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavoring agent, or printing ink. Any material used in preparing any dosage unit form is preferably pharmaceutically pure and substantially non-toxic in the amounts employed. In addition, the crystalline Form I may be incorporated into sustained-release preparations and formulations. Administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients, for example, for oral, topical, or parenteral administration, include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the crystalline Form I of nicotinamide riboside chloride in the pharmaceutically appropriate amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and freeze drying techniques that yield a powder of the active ingredient or ingredients, plus any additional desired ingredient from the previously sterile-filtered solution thereof.

Thus, the crystalline Form I of nicotinamide riboside chloride may be administered in an effective amount by any of the conventional techniques well-established in the medical field. For example, the administration may be in the amount of about 50 mg/day to about 50,000 mg per day. In some embodiments, the administration may be in the amount of about 250 mg/kg/day. Thus, administration may be in the amount of about 50 mg/day, about 100 mg/day, about 200 mg/day, about 250 mg/day, about 300 mg/day, about 500 mg/day, about 700 mg/day, about 800 mg/day, about 1000 mg/day, about 2000 mg/day, about 4000 mg/day, about 5000 mg/day, about 10,000 mg/day, about 20,000 mg/day, about 30,000 mg/day, about 40,000 mg/day, or about 50,000 mg/day.

Also disclosed are methods of producing such pharmaceutical compositions comprising combining any of the previously disclosed embodiments of the crystalline Form I of nicotinamide riboside chloride with a pharmaceutically acceptable excipient. Any acceptable method of combining an active agent with a pharmaceutically acceptable excipient may be used in accordance with the present methods, and those of ordinary skill in the art can readily appreciate appropriate techniques of combination. In some embodiments, the step of combination may be as simple as adding a desired quantity of the crystalline Form I of nicotinamide riboside chloride to an existing substance, such as a liquid beverage or a powdered beverage mixture. In other embodiments, the step of combination includes any technique that is conventionally used to mix active agents with excipients pursuant to preparing a pharmaceutical dosage form (for example, solid, semi-solid, liquid, or in a form suitable for inhalation), a cosmetic item (such as a powder, cream, lotion, or emollient), or a food item (for example, solid, semi-solid, or liquid).

In other aspects, the present disclosure pertains to methods comprising administering to a subject the crystalline Form I of nicotinamide riboside chloride. The administration of the crystalline Form I of nicotinamide riboside chloride may be by any of the routes described above in connection with the present pharmaceutical compositions. For example, the crystalline Form I of nicotinamide riboside chloride may be administered orally, topically, parenterally, enterally, or by inhalation. In view of the exceptional stability of the presently disclosed crystalline Form I of nicotinamide riboside chloride, the active agent may be used or otherwise prepared for any known route of administration, and any known route of administration may be used pursuant to the present methods. The crystalline Form I of nicotinamide riboside chloride may be administered in combination with a pharmaceutically acceptable excipient.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, and the like, avian species, such as chickens, turkeys, songbirds, and the like, i.e., for veterinary medical use.

The present disclosure also provides methods of preparing the crystalline Form I of nicotinamide riboside chloride. The methods may include the steps of forming a solution comprising nicotinamide riboside chloride and a polar solvent with hydrogen bonding, and cooling the combination. In some embodiments, the polar solvent with hydrogen bonding may be a polar alcohol. Exemplary polar alcohols include methanol, 1-butanol, 2-butanol, t-butyl alcohol, diethylene glycol, ethanol, ethylene glycol, glycerin, 1-propanol, 2-propanol. The polar solvent with hydrogen bonding may have high water solubility. For example, the polar solvent with hydrogen bonding may be acetone, acetonitrile, diglyme (diethylene glycol dimethyl ether), 1,2-dimethoxyethane (DME), dimethyl-formamide (DMF), dimethyl sulfoxide (DMSO), dioxane, hexamethylphosphoramide (HMPA), hexamethylphosphorous triamide (HMPT), N-methyl-2-pyrrolidinone (NMP), or pyridine. The polar solvent with hydrogen bonding may be combined with water. The solution may otherwise comprise a source of water.

In some embodiments, the formation of the solution comprises combining crude nicotinamide riboside chloride with the polar solvent with hydrogen bonding. In other embodiments, the solution is formed by making nicotinamide riboside chloride in situ in the presence of the polar solvent with hydrogen bonding.

Following the formation of the solution comprising nicotinamide riboside chloride and the polar solvent with hydrogen bonding, the cooling of the mixture may be at a temperature of about 15° C., about 10° C., about 0° C., about −10° C., about −15° C., about −20° C., or about −25° C. The cooling of the mixture may be for about 12 hours, about 18 hours, about 20 hours, about 24 hours, about 30 hours, about 36 hours, or about 40 hours.

Following the cooling step, the method may further comprise adding an anti-solvent to the cooled composition, which will now include some crystallized product. As used herein, an "anti-solvent" is any material that assists with pushing the crystalline product out of solution. An exemplary anti-solvent is methyl tert-butyl ether (MTBE). Following the addition of the anti-solvent to the cooled composition, the reaction mixture may be cooled for an additional period of time. The additional cooling period may be for about 4 hours, about 6 hours, about 10 hours, about 12 hours, about 14 hours, about 16 hours, about 18 hours, about 20 hours, or about 24 hours, and the cooling temperature may be about 15° C., about 10° C., about 0° C., about −10° C., about −15° C., about −20° C., or about −25° C.

Following the additional cooling period, the solids that result from the preceding steps may be filtered and/or rinsed, for example, with an anti-solvent, such as MTBE.

Also disclosed is crystalline Form I of nicotinamide riboside chloride that is prepared according to the above-described process. The crystalline Form I of nicotinamide riboside chloride may be prepared according to any embodiment of the process for forming the crystalline form that is disclosed herein.

The present invention is further defined in the following Examples. It should be understood that these examples, while indicating preferred embodiments of the invention, are given by way of illustration only, and should not be construed as limiting the appended claims. From the above discussion and these examples, one skilled in the art can ascertain the essential characteristics of this invention, and without departing from the spirit and scope thereof, can make various changes and modifications of the invention to adapt it to various usages and conditions.

EXAMPLES

Synthesis of Crude Nicotinamide Riboside Chloride

Numerous routes for the synthesis of crude nicotinamide riboside and its chloride salt have been published. Any known route, or any other acceptable route may be used in order to prepare the non-crystalline form of the relevant compound. Exemplary routes for the synthesis of nicotinamide riboside or its chloride salt are disclosed in the following publications: Jarman, et al., J. Chem. Soc. (1969), (2), 199-203 (chloride salt); Yang, et al. J. Med. Chem. 2007, 50, 6458-6461; U.S. Pub. No. 2007/0117765; Franchetti, et al., Bioorg Med Chem Lett. 2004 Sep. 20; 14(18):4655-8; Saunders P P, et al., Cancer Res. 1989 Dec. 1; 49(23):6593-9; Dowden J, et al., Nucleosides Nucleotides Nucleic Acids. 2005; 24(5-7):513-8; Schlenk, F., Archives of Biochemistry (1943), 3, 93-103; Freyne, et al., Carbohydr. Res., 78:235-242 (1980); Tanimori, et al., Bioorg. Med. Chem. Lett., 12:1135-1137 (2002); WO 2010/017374; Davies L C, Nucleosides & Nucleotides 14(3-5), 311-312 1995; Kam B L, et al., Carbohydrate Research, 77 (1979) 275-280; Viscontini M, et al., Volumen XXXIX, Fasciculus VI (1956)—No. 195, 1620-1631. The entire disclosures of each of the references listed above are incorporated herein by reference.

Nicotinamide riboside may be initially synthesized with a different anion than Cl⁻, for example, triflate or trifluoromethanesulfonate. Following synthesis of this alternative form of nicotinamide riboside, the initial ion may be "exchanged" out, with a chloride anion, or other anion with a higher affinity, taking its place, by means of ion-exchange chromatography. Those of ordinary skill in the art can readily appreciate how to perform ion-exchange chromatography.

Alternatively, amorphous nicotinamide riboside chloride may be acquired from commercial sources.

Preparation of Crystalline Nicotinamide Riboside Chloride

A solution was formed comprising methanol and nicotinamide riboside chloride. Following formation of the solution, the solution was cooled to −10° C. and maintained at that temperature. Over the course of the next 12-24 hours the product began to crystallize. The rate at which the crystallization occurs can be increased by seeding the solution, for example, using known techniques. Following this period, the mixture was confirmed to be a slurry, and 3 parts (this volume may be varied, for example, from 1-5 parts, depending on the amount of methanol) methyl t-butyl ether was added slowly over ~6-12 hours. The MTBE functioned as an anti-solvent in order to push the majority of product out of solution. The reaction mixture was then held at −10° C. for an additional 12 hours. The solids were then filtered and rinsed with MTBE.

The preceding reaction/cooling times were based on plant production of hundreds of kilograms. Many of the times may be reduced when performing the reaction on a smaller scale, without a dramatic effect on the morphology and physical form.

Preparation of Amorphous Nicotinamide Riboside Chloride

Experiments were performed to identify an appropriate method for preparing substantially pure samples of amorphous nicotinamide riboside chloride for use in comparison studies against crystalline Form I of that compound. In Table 3, below, QSA1, QSA2, and QSA3 were conducted to identify a solvent system for producing the amorphous sample.

TABLE 3

| Experiment | Solvent | XRPD |
| --- | --- | --- |
| QSA1 | Water | Amorphous |
| QSA2 | Dioxane/water (2:1) | Amorphous |
| QSA3 | Ethanol/water (2:1) | Oil |
| QSA4 | Water | Amorphous |
| QSA5 | Dioxane/water (2:1) | Amorphous |
| SAS11 | Dioxane/water (2:1) | Amorphous |

Pursuant to QSA1-QSA3, the compound (nicotinamide riboside chloride) was dissolved in the selected solvent system (see Table 3). The vial was exposed to liquid nitrogen and the frozen solution was then freeze dried under vacuum. The ethanol/water solvent system yielded an oil, and this sample was not used further. QSA4, QSA5 and SAS11 represent scaled up freeze drying experiments. The amorphous material of NR-Cl obtained pursuant to QSA5 and SAS11 (dioxane/water solvent system) what somewhat easier to handle (less sticky) than the amorphous material from water (QSA4). Accordingly, all experiments involving amorphous material were performed using the sample resulting from QSA5. However, SEM images were obtained using the sample obtained using the conditions described for SAS11.

Instrumentation

X-ray powder diffraction. The X-ray powder diffraction information concerning the crystalline nicotinamide riboside chloride was obtained using PANalytical X-PertPRO Multi-Purpose Diffractometer, model # PY3040. No special sample preparation was required.

SEM. Scanning Electron Microscopy images were obtained using Hitachi FE-SEM model #S-4500. No special sample preparation was required.

Infrared Spectroscopy. Fourier Transform Infrared Spectroscopy (FTIR) spectra were obtained using a Spectrum One™ FTIR instrument with universal Attenuated Total Reflection (Perkin-Elmer, Inc., Waltham, Mass.).

Differential Scanning Calorimetry (DSC)

DSC analysis was conducted on both crystalline Form I of nicotinamide riboside chloride and also amorphous nicotinamide riboside chloride, using a Model DSC822e Differential Scanning calorimeter (Mettler-Toledo GmbH, Switzerland). Various heating rates were used pursuant to the measurement of melting points of the crystalline Form I of nicotinamide riboside chloride, the results of which are shown in Table 4, below:

TABLE 4

| Heating Rate | Endothermic Peak (° C.) |
|---|---|
| 1K/min | 108.01 |
| 2K/mmn | 112.53 |
| 5K/mmn | 118.43 |
| 10K/min | 123.25 |
| 20K/min | 127.82 |

Figure 5:
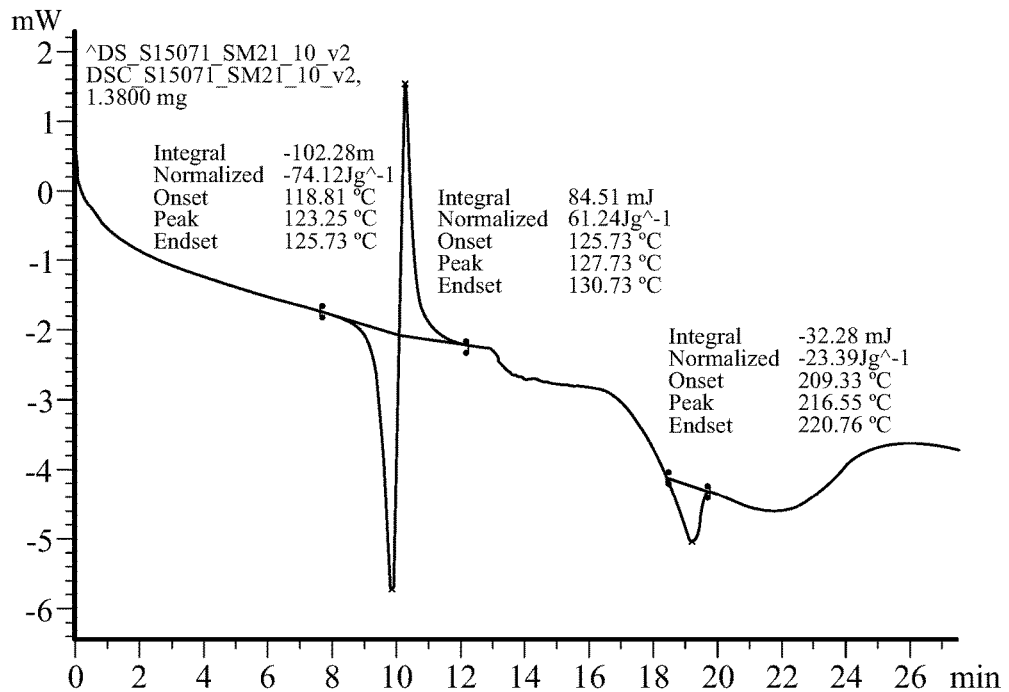
FIG. 5 provides DSC thermogram for a sample of crystalline Form I of nicotinamide riboside chloride that was heated at a rate of 10 K/min.
Figure 6:
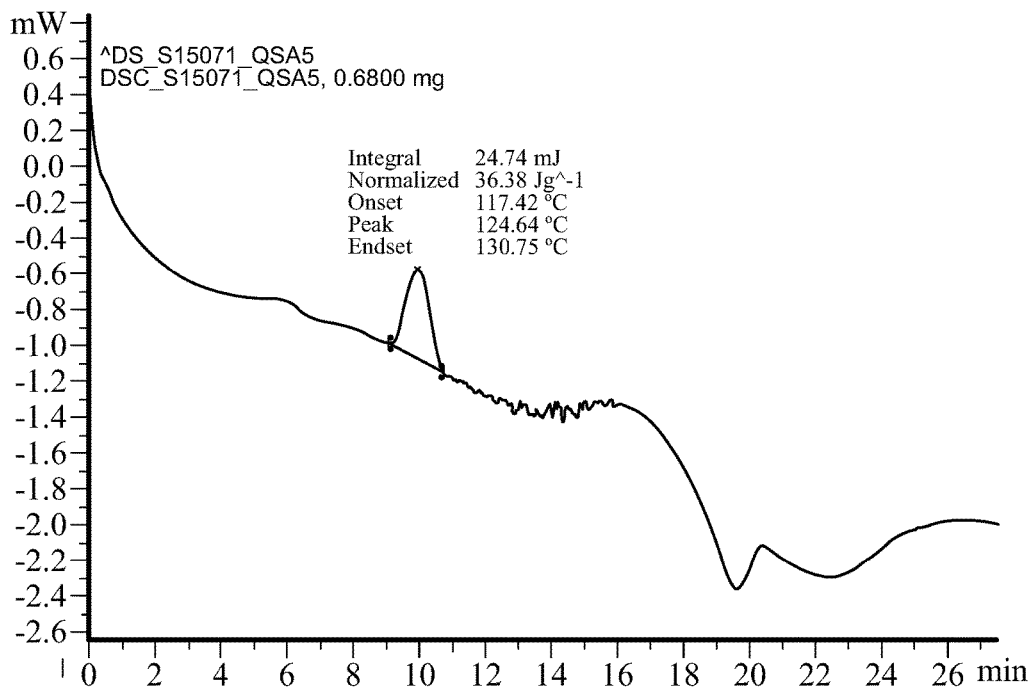
FIG. 6 provides the DSC thermogram for the amorphous form of nicotinamide riboside.

FIG. 4 provides the DSC thermograms for crystalline Form I of nicotinamide riboside chloride as measured for each of the tested heating rates. FIG. 5 provides the DSC thermagram for the sample of crystalline Form I of nicotinamide riboside chloride that was heated at a rate of 10 K/min. FIG. 6 provides the DSC thermogram for the amorphous sample. As expected, DSC analysis of the amorphous form of nicotinamide riboside chloride yielded no melting point.

Thermal Gravametric Mass Spectral Analysis

Mass loss due to solvent or water loss from the crystalline Form I of nicotinamide riboside chloride and from the amorphous form was determined by TGA/SDTA. Monitoring the sample weight, during heating in a Thermogravimetric Analysis/Simultaneous Differential Thermal Analysis (TGA/SDTA) instrument, Model 851e (Mettler-Toledo GmbH, Switzerland), resulted in respective mass vs. temperature curves.

The TGA/SDTA851e was calibrated for temperature with indium and aluminum. Samples were weighed into 100 μl aluminum crucibles and sealed. The seals were pin-holed and the crucibles heated in the TGA from 25 to 300° C. at a heating rate of 10° C. min$^{-1}$. Dry N$_2$ gas was used for purging. The gases evolved from the TGA samples were analyzed by a mass spectrometer Omnistar GSD 301 T2 (Pfeiffer Vacuum GmbH, Germany). The latter is a quadrupole mass spectrometer, which analyses masses in the range of 0-200 amu.

Figure 7B:
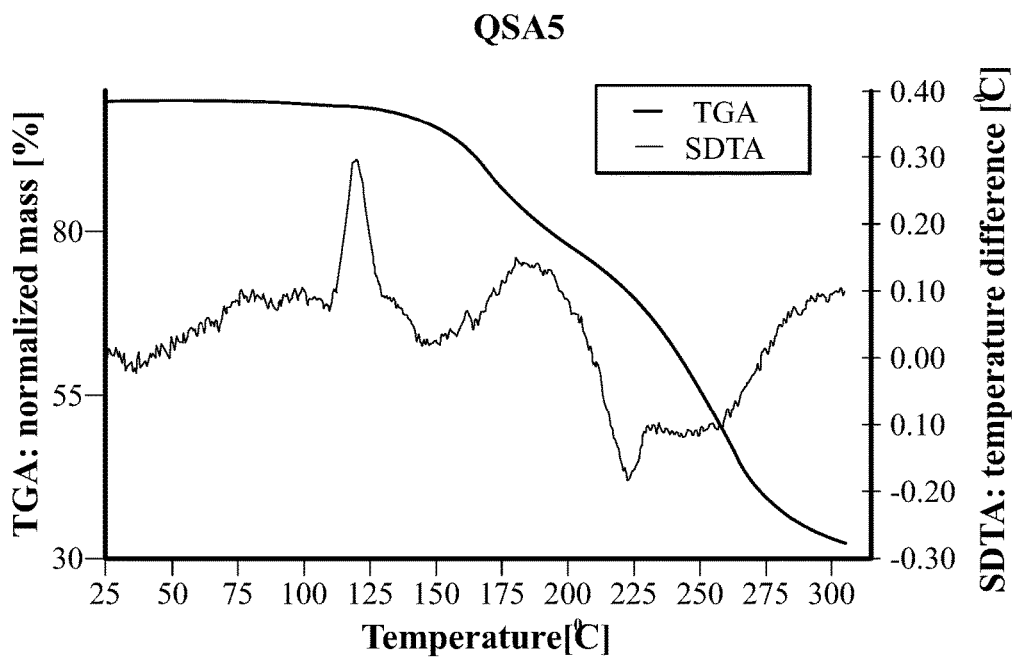
FIG. 7B shows a TGA/SDTA thermogram for the amorphous form of nicotinamide riboside.

The TGA/SDTA thermagrams for crystalline Form I of nicotinamide riboside chloride and for the amorphous form of nicotinamide riboside chloride are shown in FIGS. 7A and 7B, respectively. In FIG. 7A, the SDTA measurement for the crystalline Form I shows an endothermic event at 116.3° C., and the TGA measurement shows a mass loss of 0.36%. These results permit the conclusion that the compound is not solvated and contains a minor amount of residual solvent. In FIG. 7B, the SDTA measurement for the amorphous sample shows an exothermic event at 118.6° C., and the TGA measurement shows a mass loss of 1.59%. These results permit the conclusion that the compound is not solvated and contains some residual solvent.

Hygroscopicity/Dynamic Vapor Sorbtion (DVS)

Figure 9A:
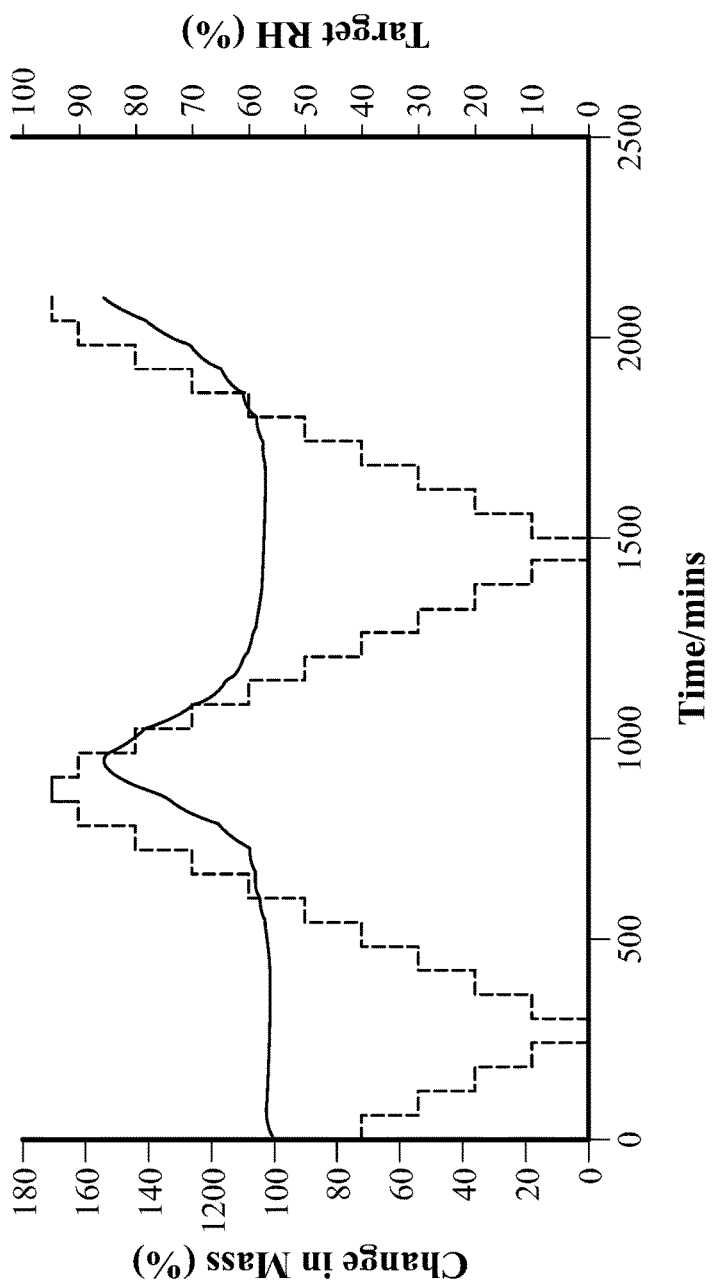
FIG. 9A provides a DVS change in mass plot for a sample of the amorphous form of nicotinamide riboside chloride, and FIG. 9B provides a DVS isotherm plot for a sample of the amorphous form of nicotinamide riboside chloride.
Figure 9B:
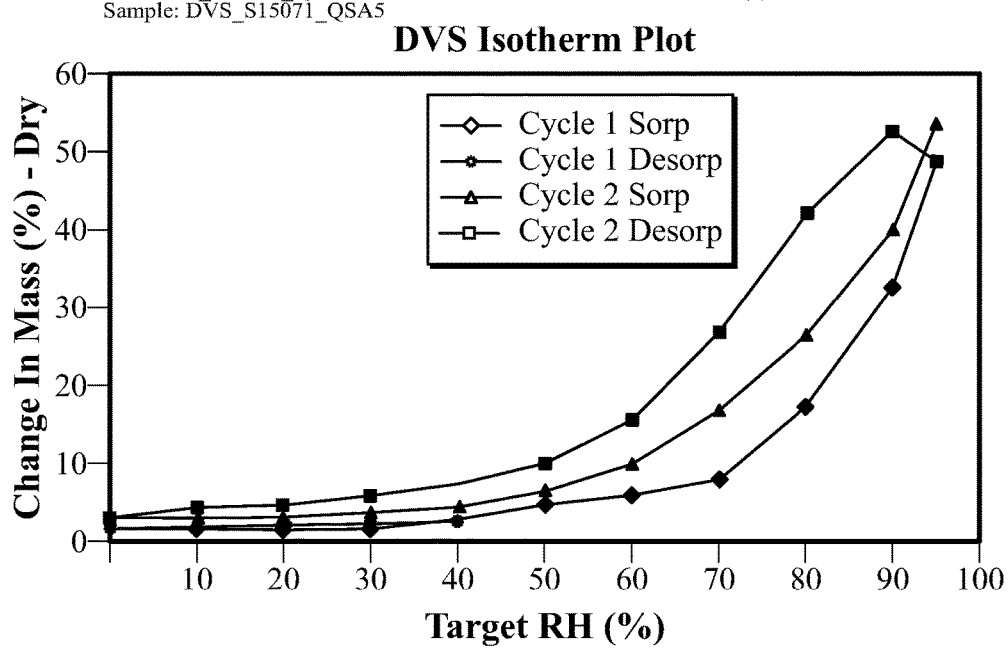

Moisture sorption isotherms were collected on a DVS-1 system from Surface Measurement Systems UK Ltd. (London, UK) for both crystalline Form I of nicotinamide riboside chloride and for the amorphous form of nicotinamide riboside chloride. Sample sizes were between 9.7 and 14.3 mg of solid material. The relative humidity was started with an initial drying step going from 40% RH to 0% RH. Subsequently, the relative humidity was increased to 95% (sorption), decreased to 0% RH (desorption) and increased again to 95% RH (sorption). Weight equilibration was set per step with a holding time of 1 hour (10% relative humidity step). Individual samples sizes were 12.6568 mg for crystalline Form I and 9.6799 mg for the amorphous sample. FIG. 8A provides a DVS change in mass plot for a sample of the crystalline Form I of nicotinamide riboside chloride, and FIG. 8B provides a DVS isotherm plot for a sample of the crystalline Form I of nicotinamide riboside chloride. FIG. 9A provides a DVS change in mass plot for a sample of the amorphous form of nicotinamide riboside chloride, and FIG. 9B provides a DVS isotherm plot for a sample of the amorphous form of nicotinamide riboside chloride.

Figure 10:
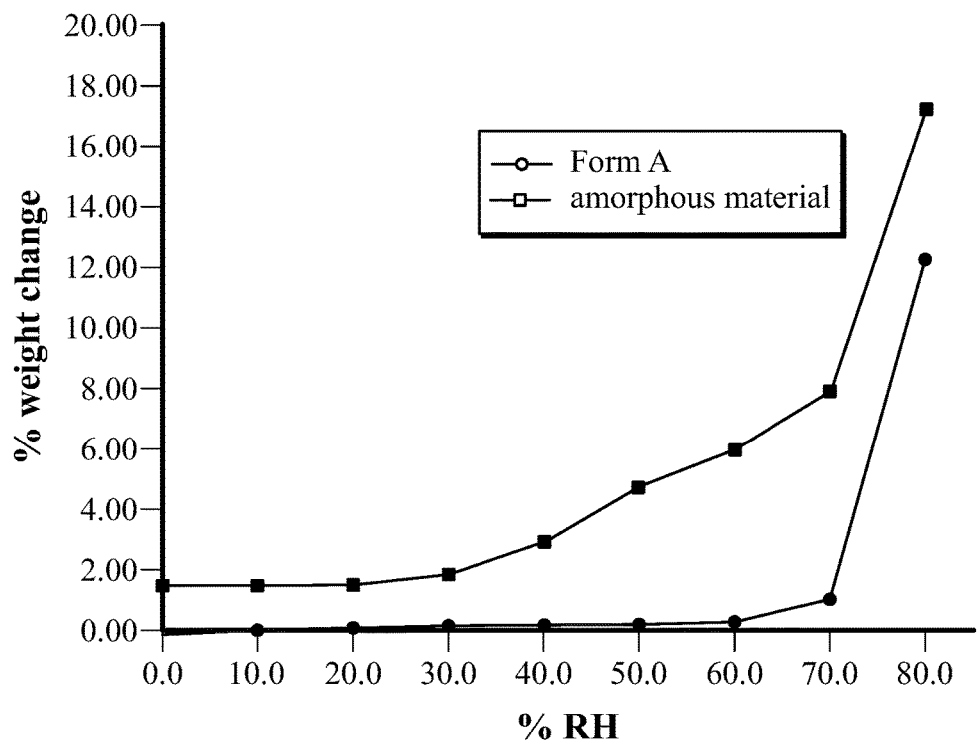
FIG. 10 provides a comparison of the sorption curve for crystalline Form I of nicotinamide riboside chloride with the sorption curve for an amorphous sample of nicotinamide riboside chloride.

FIG. 10 provides a comparison of the sorption curve for crystalline Form I of nicotinamide riboside chloride with the sorption curve for the amorphous sample. The comparison reveals that although both forms absorbed water, there was a clear difference at the rate of absorbtion from 0% to 60% relative humidity—the crystalline Form I was much less prone to absorption at lower relative humidities than the amorphous material. Even at 70% relative humidity, the weight of the crystalline sample had not increased by more than about 1.0%. These characteristics of the crystalline Form I are advantageous for the handling of the material overall and represent the ability to remain stable over a greater range of working conditions relative to the amorphous form.

What is claimed:

1. A crystalline Form I of nicotinamide riboside chloride according to formula I

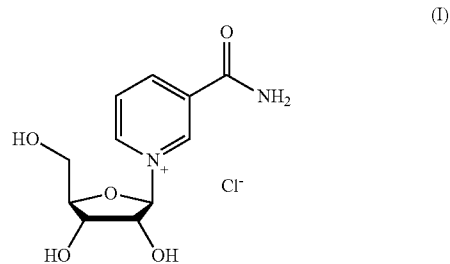

(I)

that is characterized by a powder X-ray diffraction pattern having peaks at 5.1, 15.7, and 21.7 degrees two theta ±0.2 degrees two theta.

2. The crystalline Form I according to claim 1 that is characterized by a powder X-ray diffraction pattern substantially as shown in FIG. 1.

3. The crystalline Form I according to claim 1 that is characterized by a powder X-ray diffraction pattern having peaks substantially as shown in Table 1 ±0.2 degrees two theta.

4. The crystalline Form I according to claim 1 that is characterized by an IR spectrum having peaks at 671.7, 1035.6, and 1061.8 cm$^{-1}$±0.2 cm$^{-1}$.

5. The crystalline Form I according to claim 1 that is characterized by an IR spectrum substantially as shown in FIG. 2.

6. The crystalline Form I according to claim 1 that is characterized by an IR spectrum having peaks substantially as shown in Table 2 ±0.2 cm$^{-1}$.

7. The crystalline Form I according to claim 1 that is further characterized by a DSC thermogram substantially as shown in FIG. 4.

8. The crystalline Form I according to claim 1 that is further characterized by a DSC thermogram obtained using a heating rate of 10 K/min comprising an endothermic event with an onset temperature of 119° C.±2° C., an endothermic event with a peak temperature of 123° C.±2° C., or both.

9. The crystalline Form I according to claim 1 that is further characterized by a DSC thermogram obtained using a heating rate of 1 K/min comprising an endothermic event with an onset temperature of 104° C.±2° C., a peak temperature of 108° C.±2° C., or both.

10. The crystalline Form I according to claim 1 that is further characterized by a DSC thermogram obtained using a heating rate of 2 K/min comprising an endothermic event with an onset temperature of 109° C.±2° C., a peak temperature of 113° C.±2° C., or both.

11. The crystalline Form I according to claim 1 that is further characterized by a DSC thermogram obtained using a heating rate of 5 K/min comprising an endothermic event with an onset temperature of 114° C.±2° C., a peak temperature of 118° C.±2° C., or both.

12. The crystalline Form I according to claim 1 that is further characterized by a DSC thermogram obtained using a heating rate of 20 K/min comprising an endothermic event with an onset temperature of 122° C.±2° C., a peak temperature of 128° C.±2° C., or both.

13. The crystalline Form I according to claim 1 that is further characterized by a TGA/SDTA thermogram substantially as shown in FIG. 7A.

14. The crystalline Form I according to claim 1 that is further characterized by a TGA/SDTA thermogram comprising an endothermic event at 116° C.±2° C. and a mass loss of about 0.4%.

15. The crystalline Form I according to claim 1 that is further characterized by a DVS change in mass plot substantially as shown in FIG. 8A.

16. The crystalline Form I according to claim 1 that is further characterized by a DVS isotherm plot substantially as shown in FIG. 8B.

17. The crystalline Form I according to claim 1 that is further characterized by a water vapor sorption isotherm showing a water uptake of not more than about 0.5 wt % at a relative humidity of up to 60%.

18. The crystalline Form I according to claim 1 that is further characterized by a water vapor sorption isotherm showing a water uptake of not more than about 1.0 wt %, at a relative humidity of up to 70%.

19. The crystalline Form I according to claim 1 wherein said crystalline Form I is anhydrous.

20. A method for increasing nicotinamide adenine dinucleotide (NAD) concentration in a subject in need thereof comprising administering to the subject a pharmaceutically acceptable amount of the crystalline Form I according to claim 1.

21. The method according to claim 20 wherein said crystalline Form I is administered to said subject in a composition that further comprises a pharmaceutically acceptable excipient.

22. The method according to claim 20 wherein said administration provides increased insulin sensitivity, enhancement of sirtuin function, improved mitochondrial health or function, increased production of mitochondria, or neuroprotection.

23. A method for supplementing the diet of a subject comprising administering to the subject a pharmaceutically acceptable amount of the crystalline Form I according to claim 1.

* * * * *